United States Patent [19]

Leach

[11] 3,998,892
[45] Dec. 21, 1976

[54] PREPARATION OF PREHNITENOL
[75] Inventor: Bruce E. Leach, Ponca City, Okla.
[73] Assignee: Continental Oil Company, Ponca City, Okla.
[22] Filed: Nov. 17, 1975
[21] Appl. No.: 632,335
[52] U.S. Cl. .................. 260/621 E; 260/624 E; 260/621 D
[51] Int. Cl.$^2$ .......................................... C07C 39/06
[58] Field of Search ....... 260/621 E, 621 D, 621 R, 260/624 E

[56] References Cited
UNITED STATES PATENTS

| | | | |
|---|---|---|---|
| 2,295,675 | 9/1942 | Meharg | 260/621 D |
| 3,417,149 | 12/1968 | Neworth et al. | 260/621 D |
| 3,655,778 | 4/1972 | Kuhn | 260/619 R |

FOREIGN PATENTS OR APPLICATIONS

| | | | |
|---|---|---|---|
| 1,813,647 | 9/1970 | Germany | 260/621 E |

*Primary Examiner*—James O. Thomas, Jr.
*Assistant Examiner*—W. B. Lone
*Attorney, Agent, or Firm*—Bayless E. Rutherford, Jr.

[57] ABSTRACT

Prehnitenol (2,3,4,5-tetramethylphenol) is prepared by reacting pentamethylphenol with phenol in the liquid phase using a catalyst selected from the group consisting of activated carbon, magnesium oxide and calcium oxide.

5 Claims, No Drawings

PREPARATION OF PREHNITENOL

FIELD OF THE INVENTION

The invention is in the general field of preparation of 2,3,4,5-tetramethylphenol (prehnitenol).

BACKGROUND

Prehnitenol is useful as an antioxidant in lubricating oils. Previously, it has been a component in coal tar bottoms and in the bottoms product of methylation of phenol. It can be recovered from these materials by known fractionation techniques.

I have discovered that prehnitenol can be prepared by the disproportionation (or reaction) of pentamethylphenol with phenol using certan specific catalysts. My process is unusual in that it produces a product mixture containing 2,3,4,5-tetramethylphenol in amounts several times the combined amounts of 2,3,4,6-tetramethylphenol and 2,3,5,6-tetramethylphenol.

BRIEF SUMMARY OF THE INVENTION

Briefly stated, the present invention is directed to a process for preparing 2,3,4,5-tetramethylphenol by reacting pentamethylphenol with phenol in the liquid phase in the presence of a catalyst selected from the group consisting of activated carbon, magnesium oxide and calcium oxide.

More specifically, the present invention is directed to a process for reacting pentamethylphenol with phenol in the liquid phase in the presence of a catalyst, selected from the group consisting of activated carbon, magnesium oxide and calcium oxide, to produce a product mixture containing a significant amount of 2,3,4,5-tetramethylphenol. The process is characterized further in that the product mixture contains an amount of 2,3,4,5-tetramethylphenol which is greater (usually by several fold) than the combined amounts of 2,3,4,6-tetramethylphenol and 2,3,5,6-tetramethylphenol.

DETAILED DESCRIPTION

While pure pentamethylphenol can be used, usually because of lack of availability, there will be used materials such as the bottoms product from methylation of phenol. This material can be described as a product consisting essentially of a mixture of methyl-substituted phenols containing at least 10 weight percent, preferably at least 30 weight percent, pentamethylphenol.

Any commercial grade phenol is suitable in the process.

Any ratio of phenol to pentamethylphenol can be used. However, in order to obtain better yields it is desirable to use at least a stoichiometric amount of phenol. Amounts above stoichiometric (e.g., 2:1) are more suitable since still better results are obtained. Generally, it is not desirable to use above a 3:1 stoichiometric amount since the results do not justify the increased cost.

Suitable catalysts for use in my process include activated carbon, magnesium oxide and calcium oxide. The preferred catalysts are activated carbon and magnesium oxide.

A suitable amount of catalyst is in the range of about 0.1 to about 5 weight percent based on the total amount of the phenol and pentamethylphenol. On the same basis the preferred amount of catalyst is in the range of about 0.5 to about 2 weight percent.

PROCESS CONDITIONS

A suitable temperature for conducting the process is in the range of about 375° to about 500° C. Preferably, the temperature is in the range of about 400° to about 450° C.

The process is conducted under sufficient pressure to maintain the reactants in a liquid phase. Usually, a pressure in the range of about 30 to about 125 atmospheres is suitable.

The process can be conducted on a batch or continuous basis.

Knowing the conditions stated hereinbefore any person skilled in the art can readily determine the optimum reaction time.

Usually, in a continuous process, the residence time is at least 5 minutes.

Also, usually, in a batch process, the reaction time is in the range of about 30 minutes to about 2 hours.

On completion of the reaction the product mixture is allowed to come to ambient conditions. If desired, the 2,3,4,5-tetramethylphenol can be separated from the product mixture by known fractionation and separation techniques, such as vacuum distillation and solvent extraction.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

The following were added to a 300 ml autoclave:
Phenol — 50 grams
Distillate cut rich in
pentamethylphenol — 50 grams
Activated carbon — 1 gram The autoclave was evacuated. The temperature was increased to 410°–415° C. and a maximum pressure of 37 atm. was observed at these conditions.

Samples of reaction product were taken at 1, 2 and 3 hours (termination of reaction).

The composition of the initial change and of these samples is shown in the following table. The analysis was made by GLC (gas liquid chromatography).

Table I

| Component | Weight Percent | | | |
| | | Product | | |
| | Initial | 1 hr* | 2 hr* | 3 hr* |
|---|---|---|---|---|
| phenol | 52.6 | 29.6 | 29.0 | 32.5 |
| o-cresol | 0.2 | 15.1 | 19.0 | 23.6 |
| m,p cresol |  | 0.4 | 0.3 | 0.3 |
| 2,6 xylenol |  | 2.4 | 3.8 | 5.4 |
| 2,4/2,5 xylenol |  | 0.7 | 0.8 | 1.3 |
| 2,3/3,5 xylenol |  | 0.4 | 0.6 | 1.3 |
| 3,4 xylenol |  | — | — | 0.2 |

Table I-continued

| Component | Initial | Weight Percent Product 1 hr* | 2 hr* | 3 hr* |
|---|---|---|---|---|
| 2,4,6 trimethylphenol | | 0.1 | 0.3 | 0.6 |
| 2,3,6 trimethylphenol | | 0.1 | 0.1 | 0.2 |
| 2,4,5/2,3,5 trimethylphenol | | 2.5 | 3.6 | 4.3 |
| Pentamethylbenzene | | 0.6 | 0.8 | 0.8 |
| 3,4,5/2,3,4 trimethylphenol | | 4.2 | 6.2 | 7.0 |
| 2,3,4,6/2,3,5,6 tetramethylphenol | 0.4 | 4.4 | 4.0 | 3.1 |
| 2,3,4,5 tetramethylphenol | 3.0 | 21.1 | 20.6 | 14.6 |
| Pentamethylphenol | 43.7 | 18.5 | 10.7 | 4.8 |

*Some phenol and o-cresol are in vapor phase.
**Measured at 25° C after cooling to condense phenol, o-cresol.

EXAMPLE 2

The following were added to a 300 ml autoclave:
50 grams — Phenol
50 grams — Phenol methylation bottoms containing 94% pentamethylphenol
1 gram — Magnesium Oxide The autoclave was evacuated. The temperature was increased to 415° C and a maximum pressure of 68 atm. was observed at these conditions. At the end of 1 hour reaction time the reaction product was analyzed by GLC. The reaction product had the following composition.

Table II

| Component | Weight Percent |
|---|---|
| Phenol | 29.8 |
| o-Cresol | 11.5 |
| m,p-Cresol | 2.2 |
| 2,6-Xylenol | 1.3 |
| 2,4/2,5-Xylenol | 1.1 |
| 2,3/3,5-Xylenol | 0.3 |
| 3,4-Xylenol | 0.1 |
| 2,4,6-Trimethylphenol | 0.1 |
| 2,3,6-Trimethylphenol | 0.0 |
| 2,3,5/2,4,5-Trimethylphenol | 2.3 |
| 2,3,4/3,4,5-Trimethylphenol | 2.9 |
| 2,3,4,6/2,3,5,6-Tetramethylphenol | 4.3 |
| 2,3,4,5-Tetramethylphenol | 18.1 |
| Pentamethylphenol | 24.2 |
| Xanthene | 1.2 |
| High Boilers | 0.6 |
| | 100. |

Thus, having described the invention in detail, it will be understood by those skilled in the art that certain variations and modifications may be made without departing from the spirit and scope of the invention as defined herein and in the appended claims.

I claim:

1. A process for preparing 2,3,4,5-tetramethylphenol which comprises reacting phenol with pentamethylphenol in the liquid phase in the presence of an effective amount of a catalyst selected from the group consisting of activated carbon, magnesium oxide and calcium oxide, said process being characterized further in that (1) it produces a product mixture which contains an amount of 2,3,4,5-tetramethylphenol which is greater than the combined amounts of 2,3,4,6-tetramethylphenol and 2,3,5,6-tetramethylphenol, and (2) the pressure is in the range of about 30 to about 125 atmospheres and the temperature is in the range of about 375° to about 500° C.

2. The process of claim 1 wherein the amount of catalyst is in the range of about 0.1 to about 5 weight percent based on the total amount of phenol and pentamethylphenol.

3. The process of claim 2 wherein there is present at least a stoichiometric amount of phenol.

4. The process of claim 3 wherein the catalyst is activated carbon.

5. The process of claim 3 wherein the catalyst is magnesium oxide.

* * * * *